United States Patent [19]

Hoeffkes et al.

[11] Patent Number: 5,651,793
[45] Date of Patent: Jul. 29, 1997

[54] HYDROGEN PEROXIDE PREPARATIONS CONTAINING FOAM REGULATORS

[75] Inventors: Horst Hoeffkes, Duesseldorf; Winifried Neuhaus, Mettmann; Karin Nelles, Monheim, all of Germany

[73] Assignee: Henkel Kommanditgesellschaft auf Aktien, Duesseldorf, Germany

[21] Appl. No.: 619,679

[22] PCT Filed: Sep. 19, 1994

[86] PCT No.: PCT/EP94/03118

§ 371 Date: Mar. 28, 1996

§ 102(e) Date: Mar. 28, 1996

[87] PCT Pub. No.: WO95/08978

PCT Pub. Date: Apr. 6, 1995

[30] Foreign Application Priority Data

Sep. 30, 1993 [DE] Germany ................ 43 33 370.2

[51] Int. Cl.$^6$ ................................................ A61K 7/13
[52] U.S. Cl. ................ 8/406; 8/431; 8/111; 252/186.43
[58] Field of Search ................ 8/406, 431, 111; 252/186.43; 132/208

[56] References Cited

U.S. PATENT DOCUMENTS

| | | | |
|---|---|---|---|
| 3,207,698 | 9/1965 | Liebling et al. | 252/321 |
| 3,388,073 | 6/1968 | Domba | 22/321 |
| 4,685,931 | 8/1987 | Schieferstein et al. | 8/406 |
| 4,776,855 | 10/1988 | Pohl et al. | 8/406 |
| 4,902,499 | 2/1990 | Bolish, Jr. et al. | 424/70 |
| 4,927,627 | 5/1990 | Schrader et al. | 424/62 |
| 4,929,377 | 5/1990 | Emmons et al. | 252/186.43 |
| 5,143,518 | 9/1992 | Madrange et al. | 8/406 |
| 5,376,146 | 12/1994 | Casperson et al. | 8/406 |
| 5,393,305 | 2/1995 | Cohen et al. | 8/406 |

FOREIGN PATENT DOCUMENTS

| | | |
|---|---|---|
| 0287773 | 10/1988 | European Pat. Off. . |
| 0398177 | 11/1990 | European Pat. Off. . |
| 0398576 | 11/1990 | European Pat. Off. . |
| 1107207 | 1/1962 | Germany . |
| 1164095 | 2/1964 | Germany . |
| 2205461 | 8/1973 | Germany . |
| 3445549 | 6/1986 | Germany . |
| 3534147 | 4/1987 | Germany . |
| 4018259 | 12/1991 | Germany . |
| 870994 | 11/1957 | United Kingdom . |
| 91/18584 | 12/1991 | WIPO . |

*Primary Examiner*—Paul Lieberman
*Assistant Examiner*—Caroline L. Dusheck
*Attorney, Agent, or Firm*—Ernest G. Szoke; Wayne C. Jaeschke; Real J. Grandmaison

[57] ABSTRACT

A water-containing hydrogen peroxide composition having a pH of 2 to 6 for the oxidative dyeing and bleaching of hair. The composition contains an anionic surfactant, hydrogen peroxide, a water-soluble or water-dispersible, thickening polymer or copolymer containing carboxyl or carboxylate groups, and optionally a $C_{12}$–$C_{18}$ fatty alcohol ethoxylated with up to 50 moles of ethylene oxide or a hydrogenated castor oil ethoxylated with up to 50 moles of ethylene oxide, and 0.001% to 0.05% by weight of a foam regulator component consisting of polysiloxane containing fine-particle hydrophobicized silica, wherein the content of fine-particle hydrophobicized silica is from 0.5% to 20% by weight, based on the weight of the foam regulator component.

11 Claims, No Drawings

HYDROGEN PEROXIDE PREPARATIONS CONTAINING FOAM REGULATORS

BACKGROUND OF THE INVENTION

1. Field of the Invention

This invention relates to water-containing preparations of hydrogen peroxide which are particularly suitable for use as oxidant preparations for the bleaching and oxidative dyeing of hair with oxidation dyes.

The bleaching and dyeing of hair with oxidation hair dyes is generally carried out using two separately packed preparations—the bleaching cream or oxidation hair dyeing cream (A) and the oxidant preparation (B)—which are combined shortly before application and mixed by simple shaking in an application bottle and then applied to the hair as a ready-to-use bleaching or dyeing preparation. Two-compartment mixing and dispensing containers, in which components A and B are packed separately from one another in a suitable quantity ratio and which comprise a partition between the two compartments mechanically destructible from outside and a dispensing opening in one of the two compartments, have also been designed for home use. Just before application, the partition is destroyed, after which components (A) and (B) are combined and mixed by shaking or other mechanical measures. The ready-to-use hair dyeing or bleaching preparation can be removed through the dispensing opening and directly applied to the hair to be dyed.

2. Discussion of Related Art

Rapid and homogeneous mixing of the bleaching or dyeing cream (A) and the oxidant preparation (B) is very important to the success of the dyeing process. Attempts have been made to facilitate mixing, for example, by adapting the two components to one another in regard to their composition and viscosity, as proposed for example in DE 35 34 471 A1 or in DE 37 32 147.

It has now been found that considerable problems are caused not only by the differences in viscosity between the components to be mixed, but also by the fact that mixing is accompanied by excessive foaming. The excessive generation of foam is a serious obstacle to the mechanical mixing of the liquid components (A) and (B).

The generation of foam is caused above all by the fact that the oxidant preparations, generally water-containing preparations of hydrogen peroxide, contain high-foaming anionic surfactants for stabilization. These anionic surfactants are necessary to stabilize the dispersions of thickening polymers containing carboxyl and/or carboxylate groups which are present in such preparations to increase viscosity after mixing. Bleaching or oxidation dye creams often contain high-foaming anionic surfactant as well in order to to keep the fatty alcohols dispersed in the products to increase viscosity in the dispersed state. Since it is not possible to do without these high-foaming anionic surfactants for the reasons explained above, the problem arises of controlling the generation of foam during mixing of the two liquid components (A) and (B) by a suitable additive.

In addition, the preparation obtained by mixing (A) and (B)—after application to the hair—should lend itself to removal from the hair by rinsing with water accompanied by vigorous foaming contrary to the foaming behavior required for mixing.

Accordingly, the problem addressed by the present invention was to provide a water-containing $H_2O_2$ preparation (B) containing anionic surfactant and polymer containing carboxyl and/or carboxylate groups which would generate little foam on mixing with an $H_2O_2$-free, anionic-surfactant-containing aqueous bleaching and dyeing cream (A), but which after application to the hair would lend itself to removal by rinsing with water accompanied by vigorous foaming. In addition, the $H_2O_2$ preparation would be stable in storage for a few months at 45° C.

DESCRIPTION OF THE INVENTION

The present invention relates to water-containing preparations of hydrogen peroxide for the oxidative dyeing and bleaching of hair with a pH value of 2 to 6 containing an anionic surfactant, a water-soluble or water-dispersible, thickening polymer or copolymer containing carboxyl and/or carboxylate groups and optionally $C_{12}$–$C_{18}$ fatty alcohol ethoxylated with up to 50 ethylene oxide molecules or hydrogenated castor oil, characterized in that they contain a foam regulator consisting of polysiloxane containing fine-particle hydrophobicized silica in a quantity of 0.001 to 0.05% by weight and preferably in a quantity of 0.003 to 0.01% by weight, based on the preparation as a whole, the content of fine-particle hydrophobicized silica being from 0.5 to 20% by weight and preferably from 1 to 15% by weight, based on the foam regulator.

The preparations of hydrogen peroxide according to the invention are preferably present in the form of aqueous dispersions of the polymer or copolymer containing carboxyl and/or carboxylate groups, although they may additionally contain an emulsified or dispersed fatty phase. The hydrogen peroxide content is preferably from 1 to 12% by weight, based on the preparation.

A polymer or copolymer of acrylic acid or methacrylic acid is preferably used as the polymer or copolymer containing carboxyl and/or carboxylate groups. Corresponding polymers and copolymers are known per se and have long been used as thickeners for aqueous solutions. GB-A 870 994, for example, describes dispersions of copolymers of at least 10% by weight of acrylic acid lower alkyl ester, 25 to 70% by weight of methacrylic acid and up to 40% by weight of another comonomer with a solids content of 25 to 50% by weight. Copolymers of 50 to 75% by weight of ethyl acrylate, 25 to 35% by weight of acrylic acid and 0 to 25% by weight of other comonomers are known from DE-A 11 64 095.

These copolymers may be modified in their molecular weight and hence in their thickening effect by addition of crosslinking, polyunsaturated copolymerizable comonomers. Particularly effective acrylate dispersions for this purpose are known, for example, from DE-A 34 45 549 or from EP 0 398 576 A2.

The suitable polymers are generally aqueous dispersions, typically with a solids content of 20 to 30% by weight, which are stable and of low viscosity at pH values in the range from about 2 to 6. The polymer chains begin to uncoil and pass into solution as the pH value of the dilute solutions is increased by aqueous bases, for example by alkali metal hydroxide solutions (for example sodium hydroxide or potassium hydroxide), ammonia solution, alkanolamines (for example mono-, di- or triethanolamine) and the carboxyl groups are converted into salt form, the viscosity of the solution increasing. The complete ionization of the carboxyl groups and the development of viscosity are over and clear solubility in water is achieved at a pH value of around 8.

The polymers are preferably present in the preparations according to the invention in a quantity of 0.1 to 10% by weight (expressed as solids), based on the preparation. The preparations according to the invention contain anionic surfactants for stabilization. Suitable anionic surfactants are characterized by a preferably linear alkyl group or alkenyl group containing 12 to 18 carbon atoms and an anionic group attached thereto, for example an $—SO_3^{(-)}$ or $—O—(C_2H_4O)_z—SO_3^{(-)}$ group, where z=0 or may be a number of up to 20.

Examples of these preferred anionic surfactants are alkyl sulfates, alkane sulfonates, α-olefin sulfonates, alkyl polyglycol ether sulfates and alkyl polyglycol ether sulfonates. Other suitable anionic surfactants are sulfosuccinic acid monoester salts, alkyl polyglycol ether carboxylates, oleic acid sulfonates and other high-foaming anionic sulfate or sulfonate surfactants. The anionic surfactants are preferably present in the form of their alkali metal, magnesium, ammonium or mono-, di- or trialkanolammonium salts containing 2 to 4 carbon atoms in the alkanol group. They are preferably present in a quantity of 0.1 to 10% by weight, based on the preparation.

The foam regulators used in accordance with the invention for foam regulation are present in a quantity of 0.001 to 0.05% by weight and preferably in a quantity of 0.003 to 0.01% by weight, based on the $H_2O_2$ preparation as a whole. The foam regulators consist predominantly of polysiloxane or of a mixture of various polysiloxanes and 0.5 to 20% by weight and preferably 1 to 15% by weight of hydrophobicized silica.

Fine-particle hydrophobicized silica in the context of the present invention is understood to be silica which has been prepared by treatment of microfine silica by precipitation from silicate solutions, by the removal of water from silica hydrogel or by pyrogenic decomposition of silicon tetrachloride and which has been reacted in known manner with hydrophobicizing agents, for example fatty alcohols, fatty amines, waxes, but especially organochlorosilanes, as described for example in U.S. Pat. No. 3,207,698 and U.S. Pat. No. 3,388,073. A pyrogenic silicon dioxide reacted with dimethyl chlorosilane or with trimethyl chlorosilane is mentioned as an example. Other examples are the commercial products Kieselsäure-HDK-H 2000, a product of Wacker, and Sipernat-D-10 or Aerosil-R972, products of Degussa.

The specific surface of the hydrophobicized silica, as determined by the Brunauer, Emmett and Teller (BET) method, is between 50 and 600 $m^2/g$ and preferably between 110 and 180 $m^2/g$.

The polysiloxane has a viscosity in the range from 100 to 60,000 mPa.s, preferably in the range from 1,500 to 3,000 mPa.s and more preferably in the range from 2,000 to 2,500 mPa.s, as measured with a Brookfield model RVF viscosimeter, spindle No. 5, at 10 r.p.m./25° C.

Possible polysiloxanes are, for example, methyl-phenyl polysiloxanes, amino-modified silicones, fatty-acid-modified silicones, alcohol-modified silicones, polyether-modified silicones, epoxy-modified silicones or cyclic silicones as disclosed, for example, in EP 0 398 177 A2.

However, dimethyl polysiloxane is preferably used. Examples include Dow Corning 200 Fluid 1000; Abil 1000, Abil 1500, Abil 5000, products of Goldschmidt.

The foam regulators (polysiloxane+hydrophobicized silica) used in accordance with the invention for foam regulation are commercially obtainable as such, for example under the name of Dow Corning Compound DB-100.

Other typical foam regulators, for example paraffins or the end-capped fatty alkyl polyglycol ethers disclosed in DE-OS 40 18 259 A1, may optionally be present.

A preferred embodiment of the invention is a water-containing preparation of hydrogen peroxide comprising 1 to 12% by weight of hydrogen peroxide, 0.1 to 10% by weight of anionic surfactant, 0.1 to 10% by weight of a thickening polymer or copolymer containing carboxyl and/or carboxylate groups and 0.001 to 0.05% by weight and preferably 0.003 to 0.01% by weight of a foam regulator, the content of fine-particle hydrophobicized silica being from 0.5 to 20% by weight and preferably from 1 to 15% by weight, based on the foam regulator.

In addition to the required foam-regulating effect (very little foam during mixing with an $H_2O_2$-free, anionic-surfactant-containing aqueous bleaching or dyeing cream (A); abundant foam during subsequent rinsing of the hair with water), the preparations according to the invention show surprisingly high stability in storage, even at temperatures of 45° C.

As mentioned above, the hydrogen peroxide preparation according to the invention may also contain an emulsified or dispersed fatty phase for clouding and for establishing increased viscosity and better miscibility. Suitable fatty components are, for example, paraffins, vaseline, waxes, hard fats, fatty acid monoglycerides and diglycerides and, above all, linear saturated fatty alcohols, preferably cetyl and stearyl alcohol. They may be added to the preparation in a quantity of 0.5 to 5% by weight. These fatty components may be incorporated in the preparation in dispersed form or may be dispersed in the preparation by means of the anionic and nonionic surfactant.

In addition to the components mentioned, the hydrogen peroxide preparations according to the invention may contain other axiliaries in small quantities. Examples of such auxiliaries include stabilizers for the hydrogen peroxide, such as for example dipicolinic acid, quinolinic acid, polyphosphates or the acylation products of phosphorous acid known from DE-B 11 07 207, for example 1-hydroxyethane-1,1-diphosphonic acid, in a quantity of around 0.05 to 1.5% by weight buffers for adjusting a pH value of 2 to 6, preferably acidic sodium pyrophosphate ($Na_2H_2P_2O_7$)

water-soluble protein derivatives, water-soluble cationic polymers or other hair-cosmetically active components and optionally fragrances.

The bleaching or dyeing preparations (A) used to bleach or dye the hair are preferably oil-in-water emulsions (creams). They preferably contain the fatty components mentioned above, preferably cetyl and stearyl alcohol, as fatty components. The dyeing creams serve as carriers for the oxidation dye precursors dissolved therein. In the case of bleaching preparations, these oil-in-water emulsions only occasionally contain relatively small quantities of oxidation dye precursors which, in practice, compensate overly strong natural yellow and red tones of the hair. The bleaching and dyeing creams are preferably adjusted to a pH value of 8 to 11 and are mixed before application with the hydrogen peroxide preparation according to the invention.

Accordingly, the present invention also relates to a process for coloring or lightening hair with an oxidation hair dyeing cream or bleaching cream (A) in the form of an oil-in-water emulsion with a pH value of 6.5 to 11, characterized in that the oxidation hair dyeing or bleaching cream is mixed with a hydrogen peroxide preparation (B) according to the invention with a pH value of 2 to 6 in a ratio by weight of (A) to (B) of 3:1 to 1:2, the ready-to-use hair dyeing and bleaching preparation formed is applied to the hair and is rinsed out with water after a contact time of 15 to 60 minutes at room temperature.

The hydrogen peroxide preparations according to the invention may be mixed by gentle shaking in the application bottle without significant effort or long shaking times. The resulting homogeneity of the dyeing or bleaching preparations is reflected in an improved dyeing result.

Finally, the invention relates to the use of foam regulators consisting of polysiloxane with a 0.1 to 20% by weight and preferably 1 to 15% by weight content of hydrophobicized silica for foam regulation in aqueous preparations containing hydrogen peroxide and anionic surfactant.

The following Examples are intended to illustrate the invention.

Examples
1. Hydrogen peroxide preparations

|  | 1 % by weight | 2 % by weight | 3 % by weight |
|---|---|---|---|
| Hydrogen peroxide (50% in H$_2$O) | 12.0 | 12.0 | 12.0 |
| Lauryl/myristyl (70:30) 3EO ether sulfate, Na salt (28% by weight in H$_2$O) | 2.0 | 2.0 | 2.0 |
| Ethyl acrylate/methacrylic acid copolymer, 25% by weight in H$_2$O (Latekoll ®D) | 15.0 | 15.0 | 15.0 |
| Cocofatty alkyl 5 EO n-butyl ether | — | 0.5 | — |
| Dimethyl polysiloxane, viscosity 2,000 to 2,500 mPa · s, containing 10 to 20% by weight of hydrophobicized silica (Dow Corning Compound DB-100) | 0.0067 | — | — |
| 1-Hydroxyethane-1,1-diphosphonic acid | 1.0 | 1.0 | 1.0 |
| Hydrogenated ethoxylated castor oil 40 EO (Eumulgin HRE40, a product of Henkel KGaA) | 0.05 | 0.05 | 0.05 |
| Water | ad 100 | ad 100 | ad 100 |

(EO: Ethylene oxide)

Preparation 1 corresponds to the invention while preparations 2 and 3 are intended for comparison. Preparation 2 contains an end-capped fatty alkyl polyglycol ether as foam regulator; preparation 3 does not contain a foam regulator.

| Typical oxidation hair dyeing cream | |
|---|---|
| C$_{12/18}$ fatty alcohol mixture | 11.0% by weight |
| Lauryl/myristyl (70:3) 3 EO ether sulfate, Na salt (28% by weight in water) | 25.0% by weight |
| p-Aminophenol hydrochloride | 0.5% by weight |
| p-Tolylenediamine sulfate | 0.38% by weight |
| Resorcinol | 0.25% by weight |
| p-Amino-o-cresol | 0.33% by weight |
| Sodium sulfite | 1.0% by weight |
| Ammonium sulfate | 0.7% by weight |
| Fragrance | 0.2% by weight |
| Water (and NH$_3$ to pH = 9.5) | ad 100% by weight |

Quantities of 50 ml of hydrogen peroxide preparations 1, 2 and 3 were poured into flexible 100 ml polyethylene application bottles. The oxidation hair dyeing cream was packed in 50 ml tubes.

To dye the hair, the contents of a tube of oxidation hair dyeing cream were squeezed into one of the application bottles containing hydrogen peroxide preparations 1 to 3. After the closure cap had been screwed on, the contents were mixed by shaking by hand. The ready-to-use dyeing preparations obtained after mixing were applied to the hair in the usual way and rinsed out with water after the contact time.

The generation of foam during mixing, the miscibility of the two components and the generation of foam during rinsing out with water were evaluated on a scale of 1 to 5:

| | 1→5 | |
|---|---|---|
| Foaming during mixing | No foam | Abundant foam |
| Miscibility of the two components | Readily miscible | Miscible only with considerable difficulty |
| Foaming during rinsing out | Abundant foam | No foam |

The results are set out in Table 1 below:

TABLE 1

| H$_2$O$_2$ Preparation 1, 2 or 3 Plus Dyeing Cream | Foaming During Mixing | Miscibility of the Two Components | Foaming During Rinsing Out |
|---|---|---|---|
| 1 | 2.0 | 2.0 | 2.0 |
| 2 | 2.0 | 2.0 | 2.0 |
| 3 | 4.0 | 4.0 | 1.5 |

It was found that comparison preparation 3 was mixed so homogeneously with the dyeing cream that no inhomogeneities could be discerned with the naked eye only after very prolonged shaking. The relatively poor mixing was clearly attributable to the vigorous foaming which impeded the mechanical movement of the liquid during shaking.

Preparation 1 according to the invention and comparison preparation 2 showed substantially the same foaming and mixing behavior during mixing with the dyeing cream.

Preparations 1 and 2 were then tested for stability in storage, another important criterion for H$_2$O$_2$ preparations.

a) Preparation 1 according to the invention was stored for 6 months at 45° C. (abbreviation for this preparation: 1 GG)

b) Comparison preparation 2 was stored for 4 months at 20° C. (abbreviation for this preparation: 2 G)

c) For comparison, comparison preparation 2 was freshly prepared (abbreviation for this preparation 2 F)

Stability in storage was tested as follows:

50 ml of the H$_2$O$_2$ preparation with 50 ml of the dyeing cream were introduced into a 120 ml application bottle. The height of the empty space from the top edge of the liquid to the shoulder of the bottle was 24 mm. After the dyeing cream had been introduced into the H$_2$O$_2$ preparation, the bottle was shaken so intensively that the entire space above the liquid was filled with foam. The remaining foam height was determined after time intervals of 10 seconds, 20 seconds, 40 seconds and 60 seconds. The results are set out in Table 2:

TABLE 2

| | Remaining Foam Height in mm | | |
|---|---|---|---|
| Time in Seconds | 1 GG | 2 g | 2 F |
| 0 | 24 | 24 | 24 |
| 10 | 0 | 10 | 3 |
| 20 | 0 | 10 | 0 |
| 40 | 0 | 10 | 0 |
| 60 | 0 | 10 | 0 |

It was found that the generation of foam during mixing was lowest in the case of the stored preparation 1 according to the invention (1 GG) and that the foam regulation capacity remained intact even after storage for 6 months at 45° C.

The testing of preparations 1 GG and 2 G for the miscibility of the two components ($H_2O_2$ preparation+dyeing cream) and foaming during rinsing out from the hair produced the following results (Table 3):

TABLE 3

| $H_2O_2$ Preparation 1 GG or 2 G Plus Dyeing Cream | Foaming During mixing | Miscibility of the Two Components | Foaming During Rinsing Out |
| --- | --- | --- | --- |
| 1 GG | 2.0 | 2.0 | 2.0 |
| 2 G | 3.0 | 2.5 | 2.0 |

This test also showed that the stored $H_2O_2$ preparation 1 according to the invention (1 GG) is superior to the comparison $H_2O_2$ preparation 2 (2 G) which was stored under milder conditions.

We claim:

1. A water-containing hydrogen peroxide composition having a pH of 2 to 6 for the oxidative dyeing and bleaching of hair, said composition comprising 0.1% to 10% by weight of an anionic surfactant, 1% to 12% by weight of hydrogen peroxide, 0.1% to 10% by weight of a water-soluble or water-dispersible, thickening polymer or copolymer containing carboxyl or carboxylate groups, and optionally a $C_{12-18}$ fatty alcohol ethoxylated with up to 50 moles of ethylene oxide or a hydrogenated castor oil ethoxylated with up to 50 moles of ethylene oxide, and 0.001% to 0.05% by weight of a foam regulator component consisting of polysiloxane containing fine-particle hydrophobicized silica, based on the weight of said composition, wherein the content of said fine-particle hydrophobicized silica is from 0.5% to 20% by weight, based on the weight of said foam regulator component.

2. A composition according to claim 1 wherein said polysiloxane has a viscosity of from 100 to 60,000 mPa.s as measured at 25° C. with a Brookfield RVF viscosimeter, spindle No. 5, at 10 r.p.m.

3. A composition according to claim 1 wherein said polysiloxane is a dimethyl polysiloxane.

4. A composition according to claim 1 comprising 0.003 to 0.01% by weight of said foam regulator, based on the weight of said composition.

5. The process of coloring or lightening hair comprising contacting the hair with a composition comprising (a) an oil-in-water hair dyeing or bleaching emulsion; and (b) an aqueous hydrogen peroxide composition having a pH of 2 to 6 comprising 0.1% to 10% by weight of an anionic surfactant, 1% to 12% by weight of hydrogen peroxide, 0.1% to 10% by weight of a water-soluble or water-dispersible, thickening polymer or copolymer containing carboxyl or carboxylate groups, and optionally a $C_{12-18}$ fatty alcohol ethoxylated with up to 50 moles of ethylene oxide or a hydrogenated castor oil ethoxylated with up to 50 moles of ethylene oxide, and 0.001% to 0.05% by weight of a foam regulator component consisting of polysiloxane containing fine-particle hydrophobicized silica, based on the weight of said composition, wherein the content of said fine-particle hydrophobicized silica is from 0.5% to 20% by weight, based on the weight of said foam regulator component, and wherein components (a) and (b) are mixed in a ratio by weight of from 3:1 to 1:2, respectively.

6. A process as in claim 5 wherein component (a) has a pH value of from 6.5 to 11.

7. A process as in claim 5 wherein said anionic surfactant is selected from the group consisting of alkyl sulfates, alkane sulfonates, $\alpha$-olefin sulfonates, alkyl polyglycol ether sulfates, alkyl polyglycol ether sulfonates, sulfosuccinic acid monoester salts, alkyl polyglycol ether carboxylates, oleic acid sulfonates and mixtures thereof.

8. A process as in claim 5 wherein the polysiloxane is selected from the group consisting of methyl-phenyl polysiloxanes, amino-modified silicones, fatty-acid-modified silicones, alcohol-modified silicones, polyether-modified silicones, epoxy-modified silicones, cyclic silicones, dimethyl polysiloxane and mixtures thereof.

9. A process as in claim 5 wherein said polysiloxane has a viscosity of from 100 to 60,000 mPa.s as measured at 25° C. with a Brookfield RVF viscosimeter, spindle No. 5, at 10 r.p.m.

10. A process as in claim 9 wherein said polysiloxane is a dimethyl polysiloxane.

11. A process as in claim 5 wherein said component (b) comprises 0.003 to 0.1% by weight of said foam regulator, based on the weight of said component (b).

* * * * *